(12) United States Patent
Plotnikov et al.

(10) Patent No.: US 9,435,766 B2
(45) Date of Patent: Sep. 6, 2016

(54) SYSTEM AND METHOD FOR INSPECTION OF COMPONENTS

(71) Applicant: General Electric Company, Schenectady, NY (US)

(72) Inventors: Yuri Alexeyevich Plotnikov, Niskayuna, NY (US); Daniel John Noonan, Middle Grove, NY (US); John Edward McLeod, Jr., Alplaus, NY (US); Alessio Andolfi, Camaiore (IT); Riccardo Catastini, Calenzano (IT)

(73) Assignee: General Electric Company, Niskayuna, NY (US)

( * ) Notice: Subject to any disclaimer, the term of this patent is extended or adjusted under 35 U.S.C. 154(b) by 269 days.

(21) Appl. No.: 14/097,829

(22) Filed: Dec. 5, 2013

(65) Prior Publication Data

US 2015/0160164 A1 Jun. 11, 2015

(51) Int. Cl.
*G01N 27/82* (2006.01)
*G01N 27/90* (2006.01)
*G01B 21/04* (2006.01)

(52) U.S. Cl.
CPC ........... *G01N 27/902* (2013.01); *G01B 21/047* (2013.01); *G01N 27/9026* (2013.01); *G01N 27/9093* (2013.01)

(58) Field of Classification Search
CPC ........... G01N 27/902; G01N 27/9013; G01N 27/9026
USPC ........................................................ 324/240
See application file for complete search history.

(56) References Cited

U.S. PATENT DOCUMENTS

| 3,831,283 | A | 8/1974 | Pagella et al. |
| 3,921,065 | A | 11/1975 | Rawlins et al. |
| 4,468,620 | A | 8/1984 | Vaerman |

(Continued)

FOREIGN PATENT DOCUMENTS

| CN | 201681125 U | 12/2010 |
| FR | 2145931 A5 | 2/1973 |
| KR | 101174211 B1 | 8/2012 |

OTHER PUBLICATIONS

Antonelli et al., "Qualification of a Frequency Scanning Eddy Current Equipment for Nondestructive Characterization of New and Serviced High-temperature Coatings", Proceedings of ASME Turbo Expo 2001, 8 Pages.

(Continued)

*Primary Examiner* — Reena Aurora
(74) *Attorney, Agent, or Firm* — Andrew J. Caruso

(57) ABSTRACT

An automatic portable inspection system includes a part holder for holding a component to be inspected and a rotary actuator coupled to the part holder. The system further includes an eddy current probe for scanning the component and providing eddy current signals. The system also includes a self-alignment unit coupled to the eddy current probe and configured to align an axis of the probe substantially perpendicular to a surface of the component and to maintain constant contact with said surface of the component. The system also includes a linear actuator coupled to the self-alignment unit, for providing movement of the eddy current probe along the X, Y and Z axes. A motion control unit is coupled to the rotary actuator and the linear actuator, for controlling the rotary actuator and the linear actuator for moving said probe about the component in accordance with a scan plan.

16 Claims, 7 Drawing Sheets

(56) References Cited

U.S. PATENT DOCUMENTS

| | | | |
|---|---|---|---|
| 4,891,986 A * | 1/1990 | Teagle | G01N 29/265 |
| | | | 324/262 |
| 4,958,438 A | 9/1990 | Hemmelgarn | |
| 5,430,376 A * | 7/1995 | Viertl | B82Y 15/00 |
| | | | 324/226 |
| 5,781,007 A | 7/1998 | Partika et al. | |
| 6,707,297 B2 | 3/2004 | Nath et al. | |
| 6,992,315 B2 | 1/2006 | Twerdochlib | |
| 7,068,029 B2 | 6/2006 | Hatcher et al. | |
| 7,206,706 B2 | 4/2007 | Wang et al. | |
| 7,659,715 B2 | 2/2010 | Briffa et al. | |
| 7,689,030 B2 | 3/2010 | Suh et al. | |
| 7,994,780 B2 | 8/2011 | Sun et al. | |
| 8,269,489 B2 | 9/2012 | Wang et al. | |
| 2006/0213274 A1 | 9/2006 | Moore et al. | |
| 2006/0229833 A1 | 10/2006 | Pisupati et al. | |
| 2007/0096728 A1 | 5/2007 | Mader | |
| 2010/0312494 A1 | 12/2010 | Korukonda et al. | |
| 2012/0098531 A1 | 4/2012 | Marceau et al. | |

OTHER PUBLICATIONS

Viswanathan et al., "Combustion Turbine (CT) Hot Section Coating Life Management", EPRI Semi Annual Report for Contract: U.S. DOE No. DE-FC26-01NT41231, Aug. 2002, 57 Pages.

Fukutomi et al., "Eddy-Current Inspection of Cracking in Land-Based Gas Turbine Blades", AIP Conference Proceedings, CP 700, Review of Quantitative Nondestructive Evaluation, vol. 23, 2004, pp. 368-373.

Krzywosz, "Eddy Current NDE System for On-Site Inspection", EPRI Technical Report 1005025, Mar. 2005, 44 Pages.

Zilberstein et al., "Quality Assessment of Refractory Protective Coatings using Multi-Frequency Eddy Current MWM-Arrays", AIP Conference Proceedings, 2006, CP820, Review of Quantitative Nondestructive Evaluation, vol. 25, pp. 1067-1074.

International Search Report and Written Opinion issued in connection with corresponding PCT Application No. PCT/US2014/064194 on Jan. 28, 2015.

Striegel, J., "Lego NXT Scanner", Mar. 21, 2009.

* cited by examiner

SYSTEM AND METHOD FOR INSPECTION OF COMPONENTS

BACKGROUND

The subject matter disclosed herein generally relates to non-destructive inspection of components. Specifically, the system relates to an on-site eddy current based inspection of coated components in rotary machines.

Inspection of components for the presence of anomalies prevents premature failures in rotary machines. Early detection of flaws in such components helps in rectification or replacement of components during regular maintenance schedule. Typical maintenance procedures for a component provided with a protective coating, includes stripping of the protective coating and conducting fluorescent penetrant inspection (FPI) to detect cracks in the base material. In addition, components such as buckets of the rotor are typically dismantled on site and are shipped to the inspection site. Conventional inspection techniques require inspection of all components even when cracks are not visible on the surface. Such requirements introduce discontinuity in operation of the machines and increase the cost of maintenance.

In a Non-Destructive Inspection (NDI) technique, data is acquired by scanning a surface of the component and defects in the component are detected by performing an analysis of the acquired data. Inspected components such as airfoils in gas turbines, and coated turbo components in locomotive diesel engines, may have 3D geometry and data acquisition from a complex surface of the component may not be satisfactory. Also, the scanning probe may not be in a perfect position during scanning, thereby generating several types of noise due to lift-off and tilting. Further, data acquisition near edges of the components is more difficult and may introduce additional noise components. Also, crack detection of the component is time consuming and can lengthen the downtime of normal operations.

Therefore, there is a need for an enhanced system and method for inspection of components.

BRIEF DESCRIPTION

In accordance with one aspect of the present system, an automatic portable inspection system is disclosed. The system includes a part holder for holding a component to be inspected and a rotary actuator coupled to the part holder. The rotary actuator provides rotation of the component. The system further includes an eddy current probe for scanning the component and providing eddy current signals. The system includes a self-alignment unit coupled to the eddy current probe and configured to align an axis of the eddy current probe substantially perpendicular to a surface of the component and to maintain constant contact with said surface of the component. The system also includes a linear actuator coupled to the self-alignment unit, for providing movement of the eddy current probe along the X, Y and Z axes. A motion control unit is coupled to the rotary actuator and the linear actuator, for controlling the rotary actuator and the linear actuator for moving said probe about the component in accordance with a scan plan.

In accordance with another aspect of the present system, an automatic on-site inspection method is disclosed. The method includes coupling a component to be inspected to a part holder and rotating the part holder via a rotary actuator, to position a surface of the component according to a scan plan to align substantially perpendicular to an eddy current probe. The method also includes aligning the eddy current probe via a self-alignment unit such that an axis of the probe is positioned substantially perpendicular to the surface of the component. The method further includes moving the probe via a linear actuator along at least one X, Y, Z linear axes to scan the surface of the component. The eddy current probe generates a plurality of eddy current signals for each of a plurality of scanned locations of the component. The method also includes controlling the linear actuator and the rotary actuator via a motion control unit.

DRAWINGS

These and other features and aspects of embodiments of the present invention will become better understood when the following detailed description is read with reference to the accompanying drawings in which like characters represent like parts throughout the drawings, wherein.

DETAILED DESCRIPTION

Embodiments of the present system relate to an inspection technique for detecting defects in components of rotary mechanical devices and engines. The technique in one example includes coupling a component to be inspected to a part holder and rotating the part holder via a rotary actuator, to position a surface of the component, facing a probe for scanning the component. The technique also includes aligning the probe via a self-alignment unit such that an axis of the probe is positioned perpendicular to the surface of the component and then actuating the probe via a linear actuator, along a plurality of linear axes to scan the surface of the component. The linear actuator and the rotary actuator in one example are controlled by a motion control unit.

Figure 1:
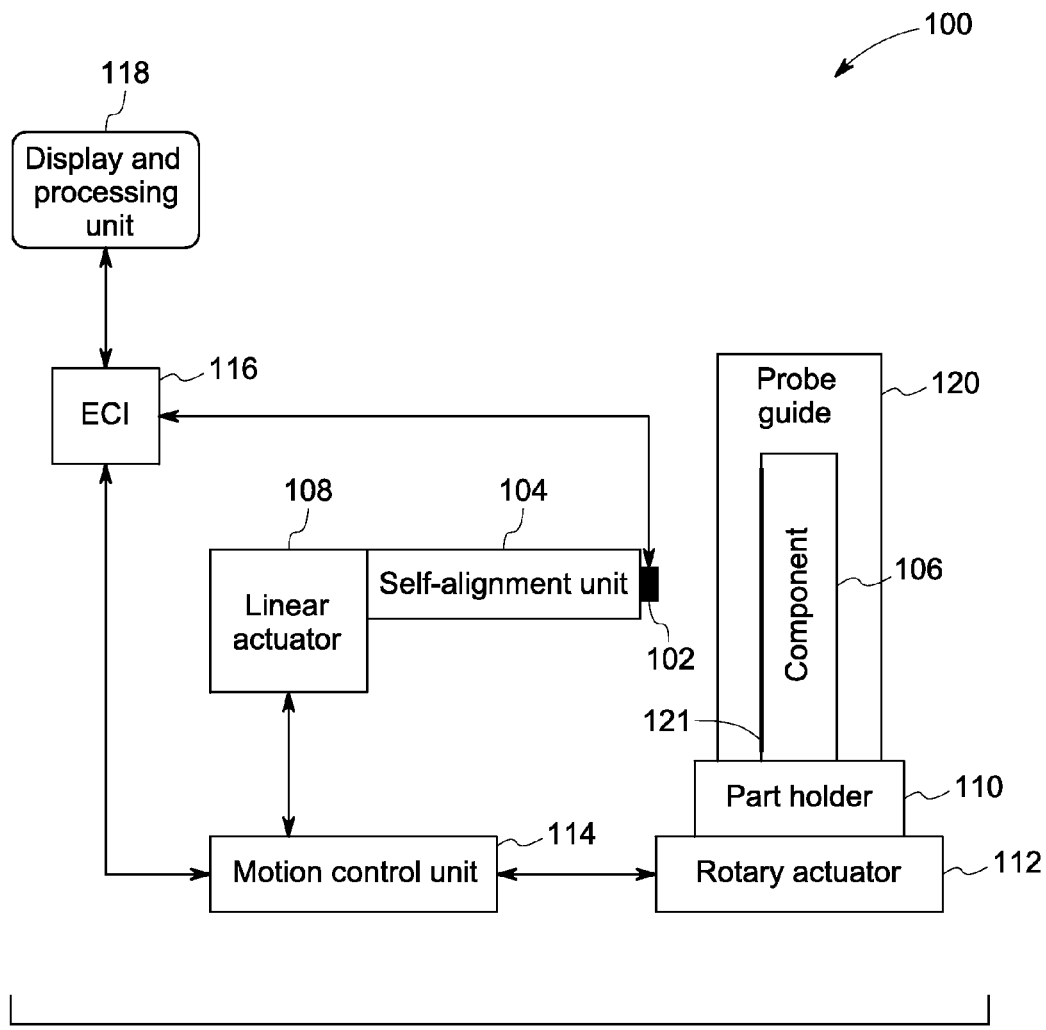
FIG. 1 is a diagrammatic illustration of an automatic portable eddy current inspection system in accordance with an exemplary embodiment.

FIG. 1 is a diagrammatic illustration of a system 100 for inspecting components using eddy current inspection techniques in accordance with an exemplary embodiment. The system 100 includes a probe 102 coupled to a self-alignment unit 104, used for scanning a component 106 under inspection. The self-alignment unit 104 is coupled to a linear actuator 108 which provides linear motion to the probe 102 along an at least one of an x-axis, a y-axis, and a z-axis. The component 106 under inspection may be, for example, an airfoil of a turbine, or a turbo component of a diesel engine, or the like. The component 106 may typically be provided with a protective coating 121 and such components may develop defects such as cracks on a surface of the component below the protective coating 121. The system 100 includes a part holder 110 for holding the component 106 to be inspected. The part holder 110 in this example is coupled to a rotary actuator 112 for rotating the part holder 110 to position a surface of the component 106, facing the probe 102 for scanning the component 106. The linear actuator 108 and the rotary actuator 112 in this example are controlled by a motion control unit 114.

In the illustrated exemplary embodiment, the probe 102 is an eddy current probe used for receiving electrical signals from an eddy current instrument (ECI) 116. The ECI 116 is also configured to receive eddy current signals from the probe 102. The ECI 116 may be a processor based device having a suitable circuitry (not shown) for generating electrical signals to be transmitted to the probe 102. The ECI 116 is coupled to sensors (not shown) to receive eddy currents generated from the probe 102 during inspection of the component 106. The ECI 116 in one example is coupled to a display and processing unit 118. The display and processing unit 118 receives eddy current signals from the ECI 116 and transmits control signals to the motion control unit 114. The display and processing unit 118 constructs an eddy current image from the eddy current signals received from the ECI 116 and performs image processing tasks such as reducing image noise. The display and processing unit 118 also displays the eddy current image and outcome of image processing tasks. The motion control unit 114 drives the probe 102 via the linear actuator 108. In alternative embodiments, at least one of the motion control unit 114 and the display and processing unit 118 may be integrated into the ECI 116. The system 100 also includes a probe runout guide 120 coupled to an edge of the component 106 for enabling the movement of the probe 102 beyond the edge of the component 106.

In one example, the linear actuator 108 and the rotary actuator 112 are coordinated and synchronized to start at a home position that establishes a known reference point to commence the scanning patterns. There are limit switches (not shown) and other mechanisms that enable the linear actuator 108 and rotary actuator 112 to have precise orientation for the scanning. The linear actuator 108 and rotary actuator 112 rotate according to the scan pattern to provide the scanning coverage of the component 106. The system 100 in such an example has a pre-defined scan pattern that commences from the home position and traverses the entire component 106 with a high density scan and with complete coverage of the entire component 106 in an efficient manner.

In alternate embodiments, the ECI 116 may include at least one controller, general purpose processor, or Digital Signal Processor (DSP). The ECI 116 may receive additional inputs from a user through a control panel or any other input device such as a keyboard of a computer system. The ECI 116 is configured to access computer readable memory modules including, but not limited to, a random access memory (RAM), and read only memory (ROM) modules. The memory medium may be encoded with a program to instruct the ECI 116 to enable a sequence of steps to generate control signals for the probe 102, the linear actuator 108, and the rotary actuator 112 so as to scan the component 106 under inspection.

According to one embodiment, the system components are shipped as a kit and easily assembled at the site for on-site inspection. The system kit components include the linear actuator 108, the rotary actuator 112, motion control unit 114, the display and processing unit 118, the ECI 116, the self-alignment unit 104, and the probe. The part holder 110 and probe runout guide 120 are typically somewhat customized to suit the component 106.

Figure 2:
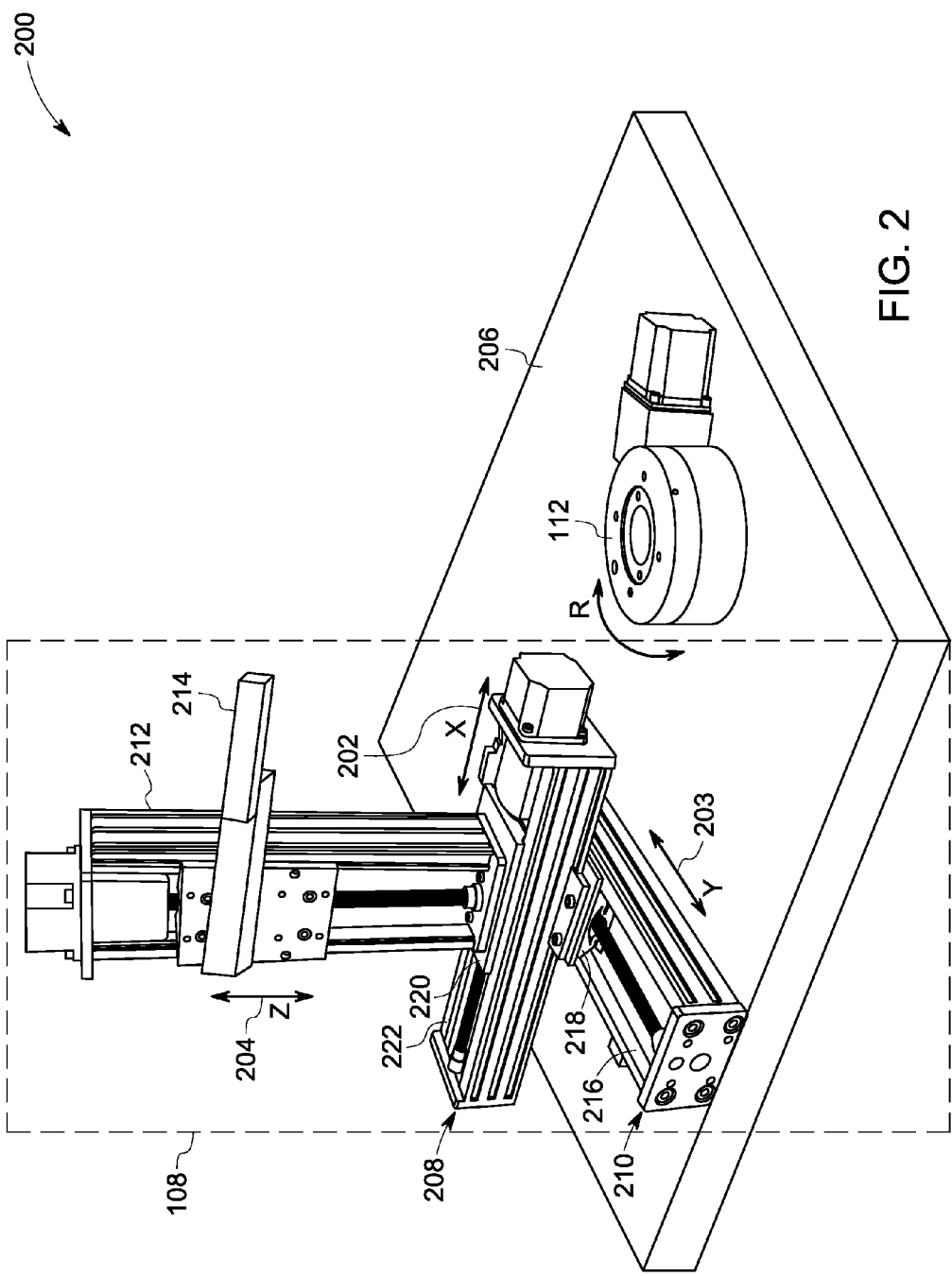
FIG. 2 illustrates a perspective view of an actuating subsystem in accordance with the exemplary embodiment of FIG. 1.

FIG. 2 is a perspective view of an actuating subsystem 200 of the system 100 (shown in FIG. 1) in accordance with an exemplary embodiment. The actuating subsystem 200 includes the linear actuator 108, and the rotary actuator 112 mounted on a platform 206. While shown as a platform 206, the platform 206 may be any relatively planar and stable base upon which the actuators 108, 112 are mechanically coupled. The actuating subsystem 200 has a compact design and in one embodiment is portable so that inspection of the component may be performed at a customer site or the on-site location of the parts to be inspected.

In the illustrated embodiment, the linear actuator 108 includes a plurality of linear guides 208, 210, 212 aligned along an x-axis 202, a y-axis 203, and a z-axis 204 respectively. Each of the plurality of linear guides 208, 210, 212 includes a fixed rail and a slider movable along the fixed rail. The guide 210 includes a slider 218 mounted movably on a fixed rail 216. The guide 208 includes a slider 220 mounted movably on a fixed rail 222. A holder 214 used for the self-alignment unit 104 (shown in FIG. 1), is mounted on the guide 212. The holder 214 mounted on the guide 212, is movable along the z-axis, thereby providing linear motion to the probe along z-axis. In the illustrated embodiment, the guide 212 is mounted on the guide 208 and is movable along the x-axis. The guide 208 is mounted on the guide 210 and is movable along the y-axis. There are a number of limit switches (not shown) that are used by the linear and rotary actuators 108, 112 to provide reference points for operation. In one example, there are limit switches on all axes of the system 200 that help to establish a home position, which is used by the motion control unit to run the scanning pattern.

Figure 3:
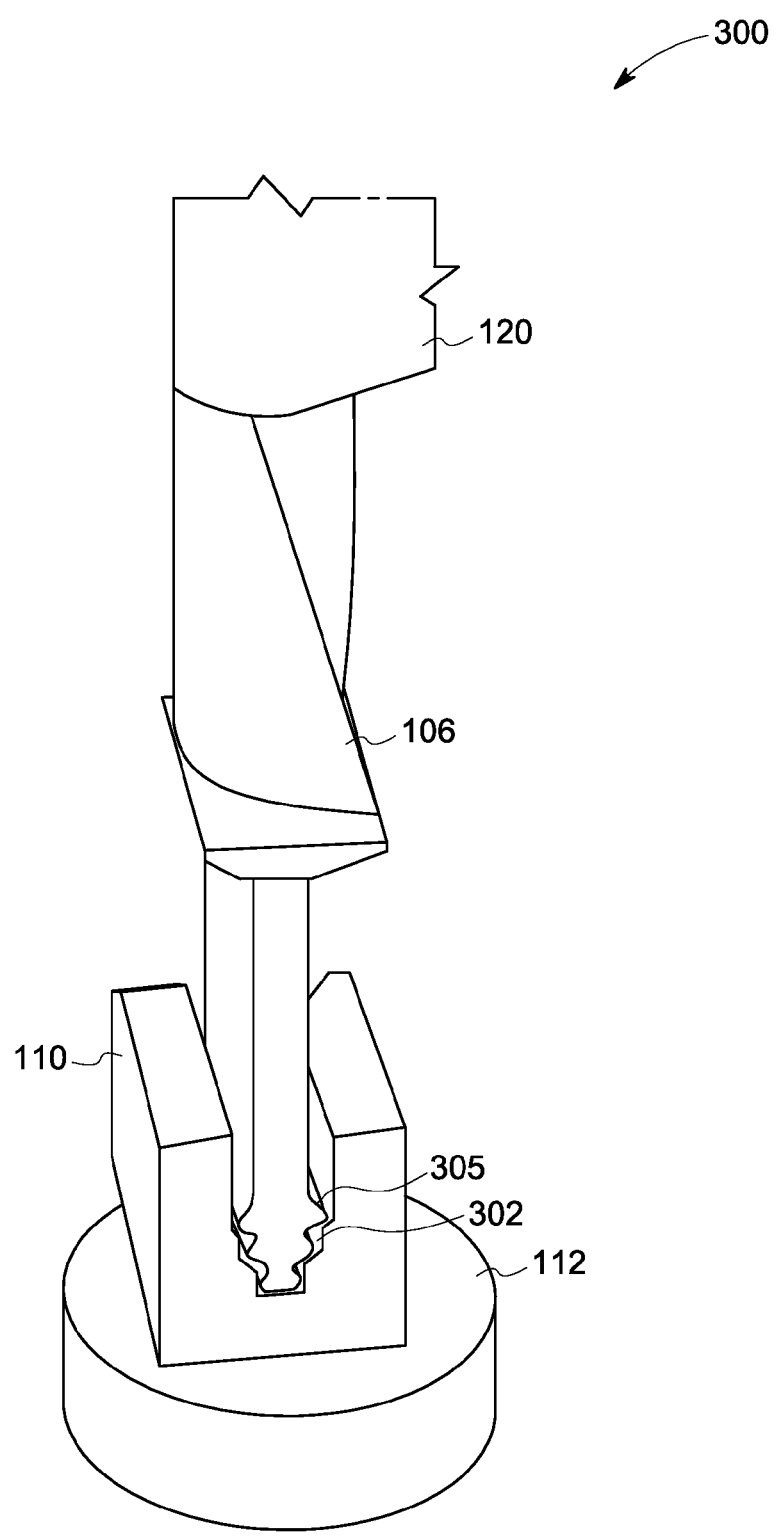
FIG. 3 illustrates a perspective view of a part holder for holding a component under inspection in accordance with an exemplary embodiment.

FIG. 3 is a perspective view illustrating a portion 300 of the system 100 (shown in FIG. 1) having the part holder 110 for holding the component 106 under inspection in accordance with an exemplary embodiment. One side of the part holder 110 is mounted on the rotary actuator 112 and another side of the part holder 110 is coupled to the component 106. In this example, the part holder 110 has a recess 302 that mates to corresponding protrusions 305 of the component 106 in order to securely hold the component 106 when the part holder 110 is rotated by the rotary actuator 112. In the illustrated embodiment, the component 106 is a bucket or blade proximate an interior of a turbine. There may be many buckets, such as 46-52 buckets, per turbine. The size and the structure of the part holder 110 are designed in such a way so as to suit the size and shape of the component 106 under inspection. In one embodiment, the part holder 110 is designed to securely hold an air foil. In another embodiment, the part holder 110 is designed to securely hold a coated component of an engine.

Figure 4:
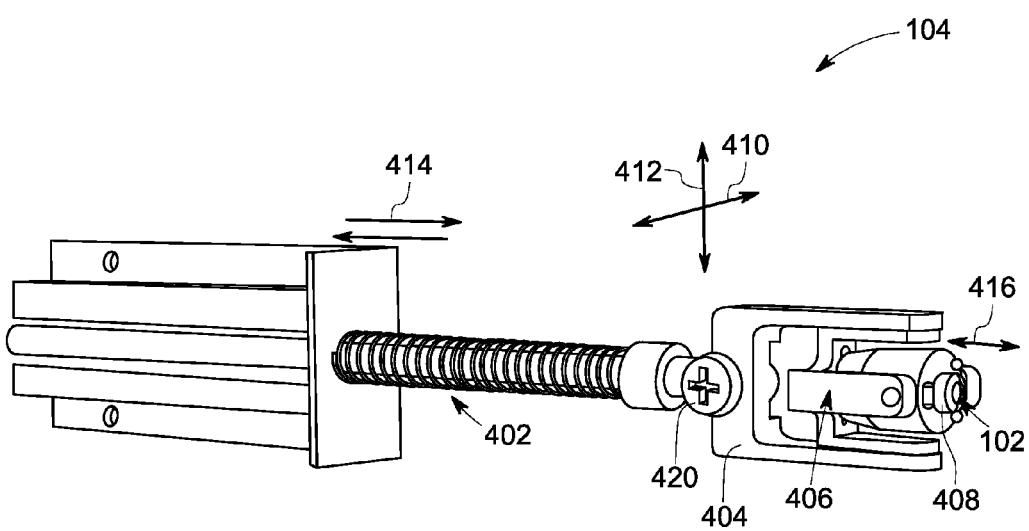
FIG. 4 illustrates a eddy current probe provided with a self-alignment unit in accordance with an exemplary embodiment.

FIG. 4 is a perspective view of a self-alignment unit 104 used to position the probe 102 approximately perpendicular to a surface of the component under inspection in accordance with an exemplary embodiment. The self-alignment unit 104 includes a spring 402 for providing pressure along a linear direction 414 so that a plurality of legs of the probe 102 firmly engage the surface of the component. The self-alignment unit 104 includes pivoting forks 404, 406 provided as rotatable supports for providing a plurality of degrees of freedom for movement of the probe 102 relative to the surface of the component. While depicted as pivoting forks 404, 406, in another embodiment gimbal bearings are employed to provide the plurality of degrees of freedom for movement of the probe 102. The first pivoting fork 404 of the self-alignment unit 104 enables one degree of movement of the probe 102 along a first direction 410. The second pivoting fork 406 enables one degree of movement of the probe 102 along a second direction 412. In this example, the first direction 410 and the second direction 412 provide two degrees of freedom for the movement of the probe 102 to detect even small cracks as the probe 102 moves along the surface of the component. A break-away pin 420 enables protection of the probe 102 and the rest of the assembly if there is excess pressure or torque. In alternative embodiments, other rotatable support mechanisms may be used in the self-alignment unit 104.

The self-alignment unit 104 further includes a spring loaded mechanism 408 that enables the probe 102 to maintain a constant contact with the surface of the component. The surface of the component may be a convex surface, a flat surface, or a concave surface. The spring loaded mechanism 408 enables to align an axis 416 of the probe 102 approximately perpendicular to the surface of the component. The structure of the spring loaded mechanism 408 is explained in further detail with reference to subsequent figures.

Figure 5:
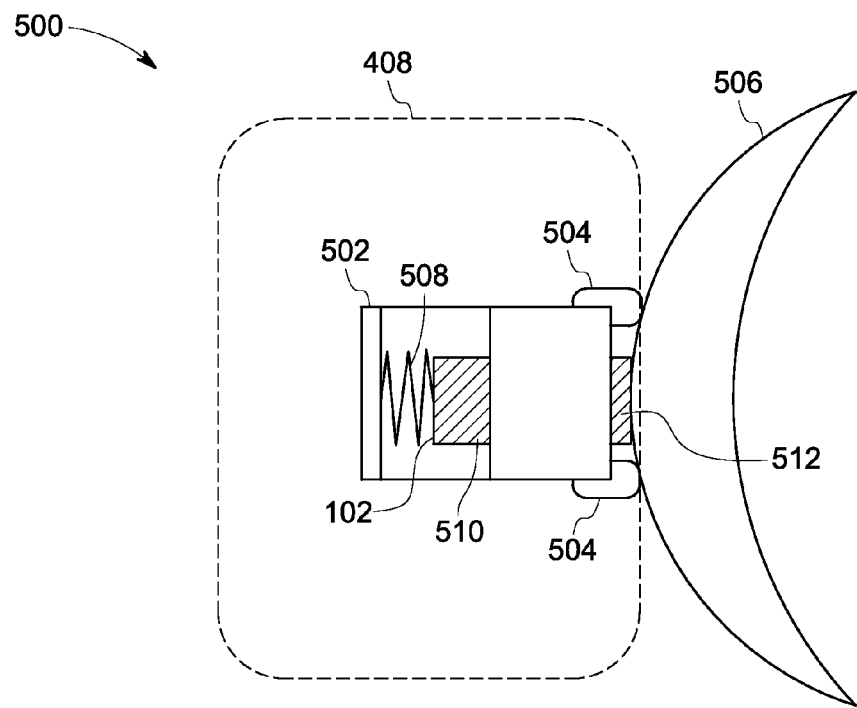
FIG. 5 is an illustration of a spring loaded mechanism for positioning a eddy current probe relative to a convex surface of a component in accordance with an exemplary embodiment.

FIG. 5 is a diagrammatic illustration 500 of the spring loaded mechanism 408 used for positioning the eddy current probe 102 relative to a convex surface 506 of the component in accordance with an exemplary embodiment. In the illustrated embodiment, the probe 102 is movably supported in a casing 502. A plurality of pins or legs 504 are coupled to the casing 502 for contacting the convex surface 506 of the component so that the probe 102 is in constant contact with the convex surface 506 throughout the scanning process. In an exemplary embodiment, three pins 504 are coupled to the casing 502 such that the pins 504 are separated from each other by an angle of about 120 degrees. In another embodiment, four pins 504 may be coupled to the casing 502 such that the pins 504 are separated from each other by an angle of about 90 degrees. In another embodiment, the legs 504 are replaced by a circular or polygonic member coupled to the casing 502, for performing the same function of holding the probe 102 in constant contact with the surface 506 of the component. The legs 504 in one example are non-rigid structures that have some amount of flexure.

A spring 508 is disposed between the casing 502 and one end 510 of the probe 102. The spring 508 provides pressure so that another end 512 of the probe 102 maintains contact with the convex surface 506 and enables movement of the probe 102 about the convex surface 506 of the component.

Figure 6:
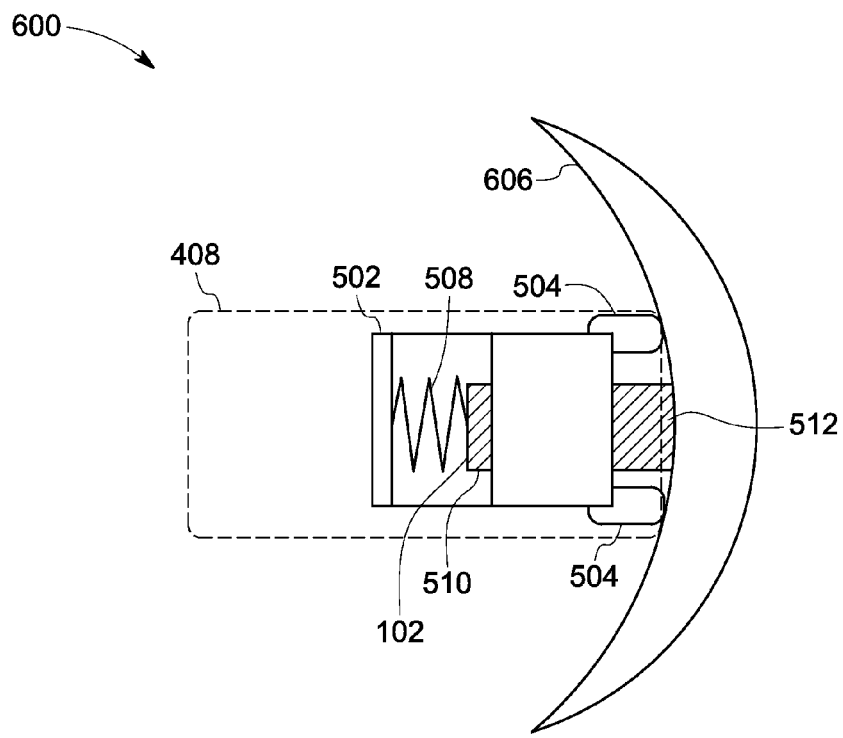
FIG. 6 is an illustration of a spring loaded mechanism for positioning an eddy current probe relative to a concave surface of a component in accordance with an exemplary embodiment.

FIG. 6 is a diagrammatic illustration 600 of the spring loaded mechanism 408 used for positioning the eddy current probe 102 relative to a concave surface 606 of the component in accordance with an exemplary embodiment. In the illustrated embodiment, the probe 102 is movably supported in the casing 502. A plurality of pins 504 are coupled to the casing 502 for contacting the concave surface 606 of the component. In an exemplary embodiment, three pins 504 are coupled to the casing 502. A spring 508 is disposed between the casing 502 and one end 510 of the probe 102, for enabling movement of the probe 102 towards and away from the concave surface 606 to maintain constant contact of another end 512 of the probe 102 with the concave surface 606.

Figure 7:
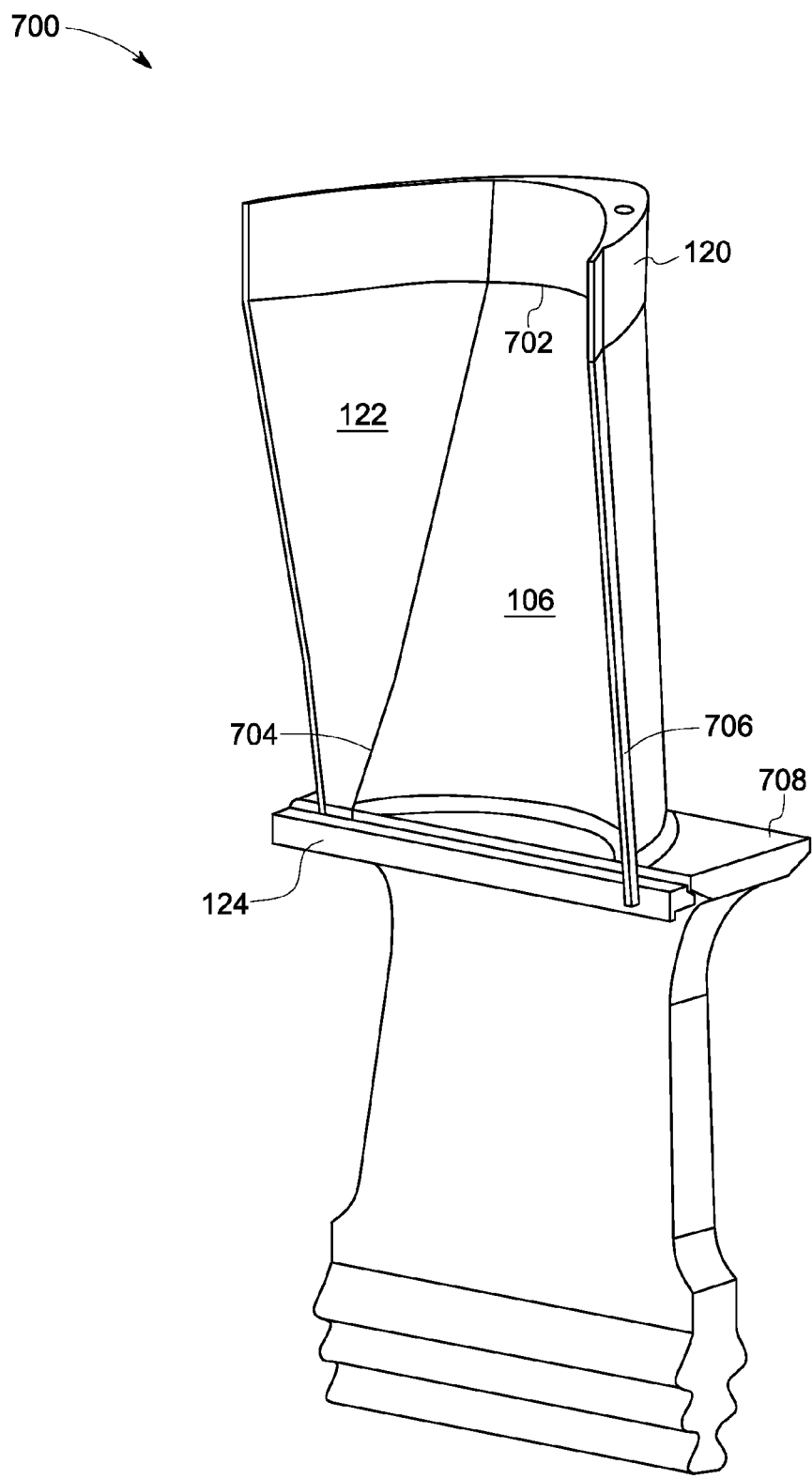
FIG. 7 is an illustration of a probe runout guide coupled to a component for enabling inspection by an eddy current probe in accordance with an exemplary embodiment.

FIG. 7 illustrates a perspective view 700 showing the probe runout guides 120, 122, 124 coupled to the component 106 (e.g. turbine blade) under inspection in accordance with an exemplary embodiment. The component 106 has an upper edge 702, a leading edge 706, a trailing edge 704 and a platform 708. The probe runout guide 120 is coupled to the upper edge 702 of the component 106, runout guide 122 is coupled to the trailing edge 704 of the component 106, and runout guide 124 is coupled to the platform 708 of the component 106. The runout guides 120, 122, 124 allow for more efficient inspection so that the probe 106 can follow the scan pattern and fully scan the component 106 including the edges. Cracks proximate the edges are difficult to detect and conventional systems would slow the processing near the edges. Such conventional scanning was slow and inefficient as the edge processing required the probe to run slower.

In this example, the component 106 is mounted on a part holder coupled to the rotary actuator such as shown in FIG. 3. According to one example, the part holder is specifically designed to mate with the particular component 106 in order to securely hold the component. The probe runout guides 120, 122, 124 in one example enables movement of the probe beyond the edges 702, 704 of the component 106 without having to slow down. In one embodiment, the probe runout guides 120, 122, 124 are made of plastic and designed to engage with the edges 702, 704 of the component 106 in order to fasten to the component 106. In alternative embodiments, the probe runout guides 120, 122, 124 may be made up of any other synthetic material. The probe runout guides 120, 122, 124 allow the probe to move smoothly beyond the edges of the component 106 under inspection without interruption. It should be noted herein that in many instances, cracks on the component 106 may grow from or towards the edges 702, 704 of the component 106. In the exemplary embodiment, the probe runout guides 120, 122, 124 maintain the quality of eddy current signals sensed by the probe at a higher signal to noise ratio (SNR). For example, for a probe having a diameter of about 0.3 to 0.8 cm, the probe runout guides 120, 122, 124 allows the probe to run beyond the edge 702 about 1 cm without changing speed of the scan. The probe runout guides 120, 122, 124 may be employed on any edges to facilitate the edge scanning in an efficient and timely manner.

Figure 8:
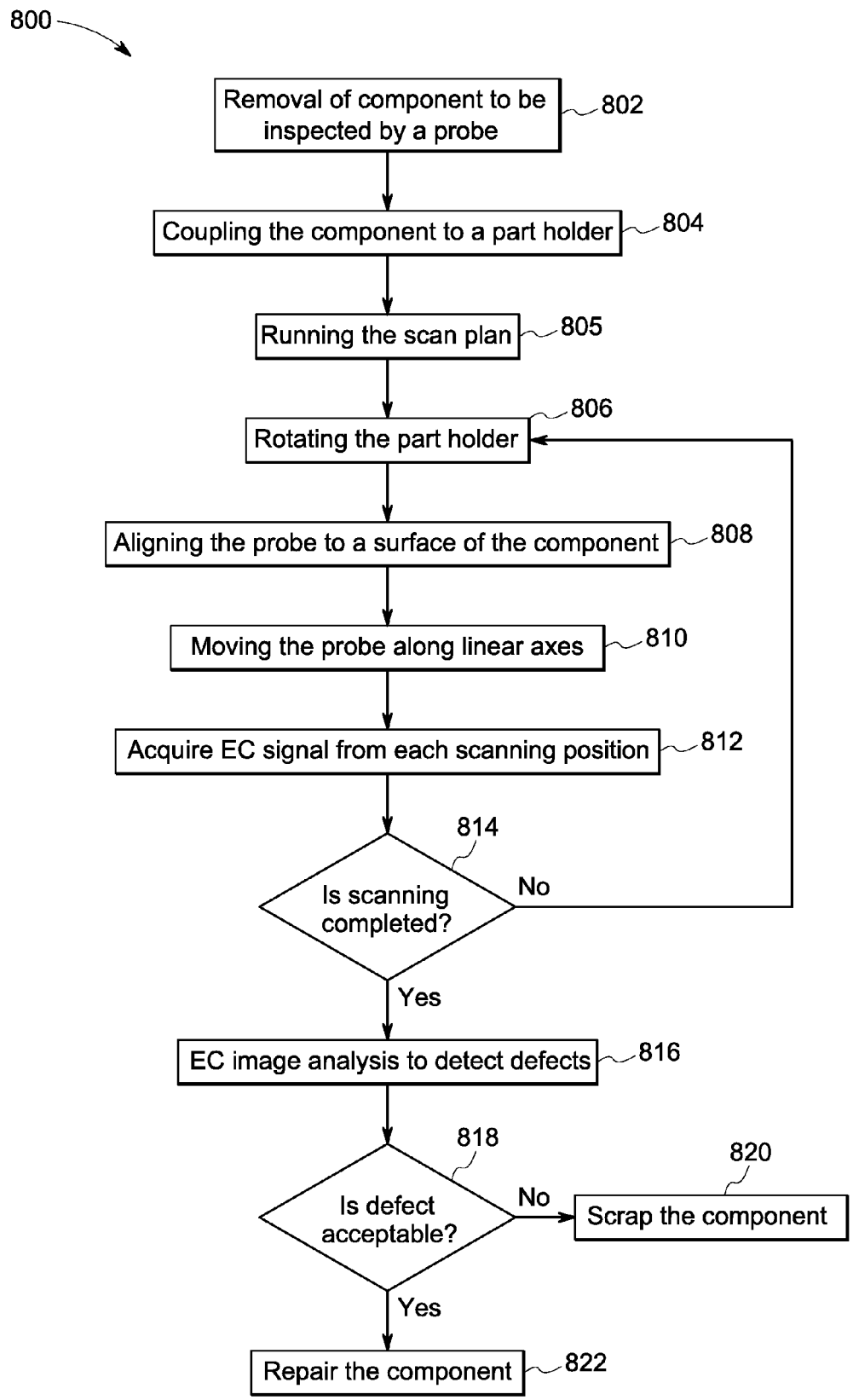
FIG. 8 is a flow chart illustrating a technique for an on-site inspection of a component in accordance with an exemplary embodiment.

FIG. 8 is a flow chart 800 illustrating the steps involved in the automatic on-site inspection method in accordance with an exemplary embodiment. The on-site inspection of the component is performed using the eddy current inspection system 100 of FIG. 1. In this example, a coated component such as an airfoil or a bucket to be inspected is removed from the on-site equipment 802 and is mounted on a stand or platform which is coupled to a part holder 804.

There is typically a scan plan developed for the component to be inspected by the probe of the eddy current inspection system. The scan plan referred to herein includes movements of the probe via the linear actuator and the rotary actuator so as to fully scan the component. The rotary actuator and the linear actuator are controlled by the motion control unit in accordance with the scan plan that involves mutual movement in the X, Y, and Z axes and the rotational direction. The scan plan is typically developed for a particular component to provide the fastest surface coverage while maintaining the probe in constant contact and substantially perpendicular to the component surface. The scan plan provides uniform eddy current coverage over the component and for construction of an eddy current image of the component.

While the process flow depicted herein is shown in sequence, the surface scan operates in accordance with the scan plan that employs at least one of the linear and rotary actuators. For example, the surface scan along the Z axis is mostly linear and can be performed at a relatively fast rate. Circumferential increments of movement for the probe are accomplished by both the rotary actuator and the linear actuator.

The process includes running the scan plan 805 that typically commences with establishing an orientation of the probe about the surface of the component. In one example, the system employs limit switches on the linear and rotary actuators so that various positions are established, such as a home position. The scan plan in one example commences from the home position and continues along the scan plan to scan the entire surface of the component. In another embodiment, the scan plan may have a plurality of home positions depending upon the area of the component to be scanned. In yet another embodiment, alternative orientation technologies are utilized to establish known reference points on the surface of the component. For example, the component may have marking or other indicia to establish reference points.

In this example, the part holder is rotated by a rotary actuator 806 to position a surface of the component to be scanned so that it is facing the probe for scanning the component in accordance with the scan plan. In one embodiment, the scan plan starts from a home positions and the part holder is rotated in accordance with the scan plan. In one example, the scan plan may specify rotation of the part holder by a fixed circumferential increment of about forty five degrees. In another example, the scan plan specifies rotating of the part holder by a circumferential increment of about ninety degrees.

The probe is aligned 808 via a self-alignment unit such that an axis of the probe is positioned approximately perpendicular to the surface of the component. During the scanning, a self-alignment unit of the eddy current probe ensures proper contact of the probe against the surface of the component. Specifically, the self-alignment unit aligns an axis of the probe approximately perpendicular to the surface of the component and the probe is held proximate to the surface.

The probe is moved 810 via a linear actuator along a plurality of linear axes to scan the surface of the component. In one embodiment, the inspection is performed by following the scan plan which includes a fast (2-10 cm/s velocity) surface scan along a z-axis of the linear actuator, typically for flat surfaces. Further, scanning of the surface of the component is performed by moving the probe along x-axis and y-axis of the linear actuator. At each scanning location of the probe along the surface of the component, an eddy current signal is acquired 812. By way of example, the scan plan can make the initial scans of relatively flat surfaces very quickly and then move more slowly during the scanning of curved surfaces.

The completion of inspection is verified 814, and the exemplary steps 806, 808, 810, 812 are repeated if the scanning is not completed or if there were errors in the scanning process.

In an exemplary embodiment, an eddy current coil having 4 mm diameter is used, with 1 mm scan increments for inspecting the entire component, such that the entirety of the component is scanned. In another embodiment, an array of eddy current sensors is used to perform the scanning of the component. To detect cracks that are smaller than the size of an eddy current coil of the probe, a 2D raster scan is employed along the y-axis. In one embodiment, the eddy current probe has a frequency range of 500 kHz-800 kHz. In another embodiment, the eddy current probe uses a combination of two frequencies (for example 500 kHz and 1200 kHz) to improve signal to noise ratio and to detect surface flaws and/or cracks under the coating at pre-defined depths of the component.

According to one scanning operation, the scanning is first performed on the flat areas of the component and then moved to the curved areas as the flat areas can be scanned at a faster speed than the curved areas.

A protective non-conductive plastic film may be provided on the sliding surface of the probe so as to protect the probe from extensive wear during mechanical scanning along the surface of the component. In an alternative embodiment, the protective non-conductive plastic film may also be disposed on the component under inspection. The probe in other examples includes slides, wheels and other protection mechanisms that allow the probe to move freely about the component surface, but protect the probe from wear.

An eddy current image generated by the inspection of the coated component is analyzed 816 by employing a suitable method among a plurality of available techniques to determine a defect such as a crack on the surface of the component. The eddy current image is constructed during or after the scan where the position of the probe on the surface corresponds to a coordinate of a pixel of the image, and the intensity and color corresponds to the eddy current signal at the corresponding point.

Image processing may be performed to reduce background noise in order to detect the presence of flaws on the surface and in the base material under the coating. In one example, a peak-to-peak subtraction in the vertical direction is performed to remove certain variations and improve the overall processing results. The image processing in one example includes at least one of low-pass filtering, band-pass filtering, and high-pass filtering.

The severity of the defect is evaluated 818 to determine reparability of the component under inspection and to check whether the defect is acceptable. In one example, a defect map is constructed to aid in the determination. The acceptability or reparability in one example is based on historical data such as field test data. The acceptability can be a range of values such as length, depth and width. Threshold operation is typically performed wherein signals above certain levels are recorded as defects.

If the severity of the crack is high, then the component is either scrapped 820 or otherwise may have to be replaced. If the defect of the component is repairable, an estimate of the cost for the repair is provided along with a repair offer to the customer. After the receipt of approval for repair by the customer, or based on prior instructions, the component is shipped to the service center. The protective coating of the component is stripped at the service center and the defect on the surface of the component is repaired 822.

A technical effect of an exemplary technique of inspecting coated component is performed using an exemplary automatic portable eddy current inspection system at a customer site thereby avoiding shipment of components to the service center. Components are inspected on-site without stripping the protective coating of the components, thereby reducing time needed for the inspection. Components with repairable defects are shipped to the service center and coating is stripped just before the repairing of the defect on the surface of the component.

The efficiency of the scan is one feature of the present system. For example, if there are about 46 buckets in one turbine, and the scan currently takes about 25 minutes to complete per bucket, then a reduction in only a few minutes per bucket saves considerable effort in testing.

The system in one example is portable and can be transported to distant customer sites for the on-site inspections. The exemplary automated inspection establishes a more objective determination as compared to subjective determinations by operators that can lead to false positives and false negatives.

According to one embodiment, the bucket or blade is removed from the rotor in-situ as compared to the depot level inspections common in the field. The bucket is inspected without removing the coating, which is another feature of the present system. The scan plan is employed to obtain the eddy current images of the component using a motion control unit to control the linear and rotary actuators. A self-alignment unit helps to maintain the probe in constant contact with the surface of the component in approximately a perpendicular direction. The scanning is performed and the processing detects surface flaws and/or cracks under the coating. If the cracks and/or surface flaws are substantial, the bucket is scrapped.

If the cracks or flaws are repairable, the component is subjected to a repair process that dispatches a repair offer. The part is then shipped or delivered to the repair shop which involves stripping the coating, repairing the component, and re-coating the component. In such a manner, only the buckets that are required to be stripped of the coating are actually stripped.

It is to be understood that not necessarily all such objects or advantages described above may be achieved in accordance with any particular embodiment. Thus, for example, those skilled in the art will recognize that the systems and techniques described herein may be embodied or carried out in a manner that achieves or improves one advantage or group of advantages as taught herein without necessarily achieving other objects or advantages as may be taught or suggested herein.

While the technology has been described in detail in connection with only a limited number of embodiments, it should be readily understood that the invention are not limited to such disclosed embodiments. Rather, the technology can be modified to incorporate any number of variations, alterations, substitutions or equivalent arrangements not heretofore described, but which are commensurate with the spirit and scope of the claims. Additionally, while various embodiments of the technology have been described, it is to be understood that aspects of the inventions may include only some of the described embodiments. Accordingly, the inventions are not to be seen as limited by the foregoing description, but are only limited by the scope of the appended claims.

What is claimed as new and desired to be protected by Letters Patent of the United States is:

1. An automatic portable inspection system, comprising:
   a part holder for holding a component to be inspected;
   a rotary actuator coupled to the part holder, wherein said rotary actuator provides rotation of the component;
   an eddy current probe for scanning the component and providing a plurality of eddy current signals;
   a self-alignment unit comprising a casing for the eddy current probe, a plurality of pins extending from the casing to a surface of the component, and a spring disposed between the casing and one end of the eddy current probe, wherein another end of the probe engages the surface of the component, wherein the self-alignment unit is coupled to the eddy current probe, wherein said self-alignment unit is configured to align an axis of the eddy current probe substantially perpendicular to a surface of the component and to maintain constant contact with said surface of the component during scanning;
   a linear actuator coupled to the self-alignment unit, wherein the linear actuator provides movement of the eddy current probe along the X, Y and Z axes; and
   a motion control unit coupled to the rotary actuator and the linear actuator, wherein said motion control unit controls the rotary actuator and the linear actuator for moving said eddy current probe about the component in accordance with a scan plan.

2. The system of claim 1, further comprising a processing unit for constructing an eddy current image from the eddy current signals.

3. The system of claim 1, wherein the motion control unit operates according to the scan plan to actuate the rotary actuator and the linear actuator, and wherein the motion control unit simultaneously controls motion of the rotary actuator and the linear actuator in accordance with the scan plan.

4. The system of claim 1, wherein the component is a bucket having a coating.

5. The system of claim 1, wherein the self-alignment unit comprises a spring loaded mechanism to provide pressure and maintain contact between the eddy current probe and the surface of the component.

6. The system of claim 1, wherein the self-alignment unit further comprises a first pivoting fork and a second pivoting fork for providing a pivot support to the probe.

7. The system of claim 1, further comprising at least one probe runout guide coupled to at least one edge of the component for enabling movement of the probe beyond the edge of the component.

8. The system of claim 1, wherein the probe scans an entirety of the component.

9. The system of claim 1, wherein the system is packaged as a kit and deployed on-site.

10. An automatic on-site inspection method, comprising:
    coupling a component to be inspected to a part holder;
    rotating the part holder via a rotary actuator, to position a surface of the component according to a scan plan to align substantially perpendicular to an eddy current probe;
    aligning the eddy current probe via a self-alignment unit such that an axis of the eddy current probe is positioned substantially perpendicular to the surface of the component by moving the eddy current probe towards and away from the surface of the component, via a spring disposed between a casing and the eddy current probe, wherein the eddy current probe is held within the casing;
    moving the eddy current probe via a linear actuator along at least one X, Y, Z linear axes to scan the surface of the component, wherein the eddy current probe generates a plurality of eddy current signals for each of a plurality of scanned locations of the component; and
    controlling the linear actuator and the rotary actuator via a motion control unit.

11. The method of claim 10, wherein the aligning comprises contacting a plurality of legs of the self-alignment unit against the surface of the component.

12. The method of claim 10, wherein the aligning comprises rotating the eddy current probe relative to the surface of the component, via at least one pivot fork of the self-alignment unit.

13. The method of claim 10, further comprising coupling a probe guide to an edge of the component and moving the eddy current probe along the probe guide beyond the edge of the component.

14. The method of claim 10, further comprising detecting cracks under a coating of the component.

15. The method of claim 10, further comprising processing the plurality of eddy current signals and constructing an eddy current image.

16. The method of claim 15, further comprising removing noise from the eddy current image by at least one of low pass-filtering, band-pass filtering, and high-pass filtering.

* * * * *